United States Patent [19]

Messing et al.

[11] 4,083,982
[45] Apr. 11, 1978

[54] PROCESS FOR PRODUCING ANALGESIA

[75] Inventors: Rita B. Messing, Irvine, Calif.; Loy D. Lytle, Concord, Mass.

[73] Assignee: Massachusetts Institute of Technology, Cambridge, Mass.

[21] Appl. No.: 783,589

[22] Filed: Apr. 1, 1977

Related U.S. Application Data

[62] Division of Ser. No. 683,983, May 6, 1976, Pat. No. 4,035,511.

[51] Int. Cl.² ............................................. A61K 31/485
[52] U.S. Cl. ................................................... 424/260
[58] Field of Search ........................................ 424/260

[56] References Cited

PUBLICATIONS

Terry et al., Fed. Proc., vol. 33, p. 560, (1974).
Fuller et al., Journal of Pharmacology & Experimental Theropeutics, vol. 19, pp. 796–803, (1975).

*Primary Examiner*—Stanley J. Friedman
*Attorney, Agent, or Firm*—Arthur A. Smith, Jr.; Robert Shaw; Paul J. Cook

[57] ABSTRACT

Analgesia is produced or hyperalgesia is reduced in an animal including human beings by administering 3-(p-trifluoromethylphenoxy)-N-methyl-3-phenylpropylamine either alone or with morphine sulfate. A novel composition is provided comprising 3-(p-trifluoromethylphenoxy)-N-methyl-3-phenylpropylamine and 25 to 50 weight percent morphine sulfate based upon the weight of the phenylpropylamine.

3 Claims, No Drawings

PROCESS FOR PRODUCING ANALGESIA

The Government has rights in this invention pursuant to Grant No. PHS-5-R01-MH25075-02 awarded by the National Institutes of Health.

This is a division of application Ser. No. 683,983 filed May 6, 1976, now U.S. Pat. No. 4,035,511.

BACKGROUND OF THE INVENTION

This invention relates to a method for producing analgesia or reducing hyperalgesia.

At the present time the common method for producing analgesia comprises administering an opiate such as morphine sulfate to the patient. While the opiates are highly effective in producing analgesia, there use is undesirable since they are addictive even when used sparingly. This disadvantage has promoted extensive research to identify alternative analgesics which are effective while being non-addictive.

It has been repeatedly demonstrated that reductions in brain serotonin produce hyperalgesia to painful stimuli in test animals. This effect is observed when serotonin reductions are accomplished by diet, or brain lesions. It also has been demonstrated that reversal of the hyperalgesia can be induced by administering through the animal brain serotonin or the amino acid precursors of serotonin, tryptophan or 5-hydroxytryptophan. These results have led to the conclusion that serotonin concentration in the brain has a direct or indirect effect on hyperalgesia and may have an effect on analgesia. However, it also has been demonstrated that the mere administration of brain serotonin or its amino acids precursors does not produce analgesia. Similarly, it has demonstrated that known compounds which inhibit serotonin uptake do not produce analgesia including chlorimipramine. Thus, for a composition to be an effective analgesic, it should have the effect of inhibiting uptake of serotonin as well as having additional effects which have not yet been identified.

It would be highly desirable to provide an otherwise innocous analgesic which could serve as a substitute for opiates in order to avoid the problems of addiction which accompany the administration of opiates.

SUMMARY OF THE INVENTION

The present invention is based upon the discovery that the compound, 3-(p-trifluoromethylphenoxy)-N-methyl-3-phenylpropylamine produces analgesia when administered to animals. This compound is admixed with an innocuous vehicle which does not degrade the compound and the mixture can be administered subcutaneously, orally, intraveneously or intramuscularly.

DESCRIPTION OF SPECIFIC EMBODIMENTS

The compounds, 3-(p-trifluoromethylphenoxy)-N-methyl-3-phenylpropylamine is available from Eli Lilly and Company, Indianapolis, Indiana. It is surprising that this compound produces analgesia in animals even though it known to inhibit the uptake of brain serotonin since other compounds which are known to have this effect do not produce analgesia. Furthermore, it has been determined that the isomer of this compound, 3-(o-trifluoromethylphenoxy)-N-methyl-3-phenylpropylamine does not produce analgesia.

While the mechanism by which 3-(p-trifluoromethylphenoxy)-N-methyl-3-phenylpropylamine produces analgesia has not yet been determined, it has been determined that its mechanism differs from the mechanism by which morphine sulfate produces analgesia. Tests have been conducted which show that known antagonists for morphine-induced analgesia are not antagonists for 3-(p-trifluoromethylphenoxy)-N-methyl-3-phenylpropylamine-induced analgesia. For example, DL-p-chloropatnylalanine HCl is a known inhibitor of the enzyme, tryptophan hydroxylase which produces the amino acids precursors to serotonin. Animals injected with the compound of this invention at dosages sufficiently high to produce analgesia exhibit a loss of the analgesia when they are subsequently administered DL-p-chlorophenylalanine HCl. In contrast, while the prior art evidence is somewhat conflicting, most studies show that serotonin depletion by DL-p- chlorophenylalanine HCl do not antagonize morphine sulfate analgesia. This evidence provides support for the proposition that the compound of this invention produces analgesia by a mechanism different from morphine sulfate.

Further evidence that the compound of this invention produces analgesia by a mechanism different from morphine sulfate results from the fact that administration of the compound, 1-N-allyl-7,8-dihydro-14-hydroxynormorphine (Naloxone) antagonizes the analgesia produced with morphine sulfate but does not antagonize the analgesia produced by the compound of this invention. Furthermore, Naloxone does not antagonize the additive effect of morphine and the compound employed in this invention.

It has been determined that the process of this invention not only inhibits the uptake of serotonin but also reduces the concentration in the brain of its metabolite, 5-hydroxyindoleacetic acid.

The administration of the compositions employed in the present invention can be effected orally, subcutaneously, intraveneously or intramuscularly. Conveniently, the compositions employed in this invention are admixed or dissolved in any innocuous vehicle such as water or sterile saline solution. When producing analgesia, the compounds employed in the present invention are administered in concentrations to avoid undesirable side effects. The compound, 3-(p-trifluoromethylphenoxy)-N-methyl-3-phenylpropylamine is employed in concentrations of between about 0.01 mg/kg body weight and 500 mg/kg body weight. Concentrations below about 0.01 mg/kg body weight do not produce significant analgesia while concentrations above about 500 mg/kg body weight do not significantly extend the time is of analgesia and may produce undesirable side effects. When employing the process of this invention, analgesia is produced for a period of about 48 hours. In addition, analgesia is abolished upon administering of at least about 150 mg/kg body weight of DL-p-chlorophenylalanine HCl.

In another aspect of this invention, it has been found that the co-administration of morphine sulfate and 3-(p-trifluoromethylphenoxy)-N-methyl-3-phenylpropylamine produces a synergistic analgesic effect over either compound when administered alone. With equal concentrations of the two compounds, the increased analgesic effect is in the order of about 60% over that obtained with either compound when administered alone. In order to obtain this synergistic effect, useful concentrations of morphine sulfate are between about 25 and about 50 weight percent based upon the weight of 3-(p-trifluoromethylphenoxy)-N-methyl-3-phenylpropylamine. It has been determined that the administration of Naloxone fails to antagonize the analgesic effect of morphine sulfate and 3-(trifluoromethylphenoxy)-N-methyl-3-phenylpropylamine. This provides further evidence that the mechansim of the action morphine sulfate and 3-(trifluoromethylphenoxy)-N-methyl-3-phenylpropylamine as employed in this invention are independent.

The following examples illustrate the present invention and are not intended to limit the same.

EXAMPLE 1

This example illustrates the analgesic effect of the compound, 3-(p-trifluoromethylphenoxy)-N-methyl-3-phenylpropylamine.

The tests described below were conducted on naive, male, Sprague-Dawley CD-derived rats obtained from the Charles River Breeding Laboratories, Wilmington, Mass. The rats weighed between 150 and 250 grams. The animals were maintained on a 12:12 hour light-dark cycle and were tested during the light portion of the cycle. Flinch or jump responses to presentations of electric foot shocks were determined by the method of Evans, Psychopharmacolgia, Vol 2, Pg. 318, (1961). Animals were introduced into a sound-attenuated test apparatus and given six alternating ascending and decending series of ten shocks of 0.2 seconds duration. The shocks (0.1. 0.2, 0.4, 0.6, 0.8, 1.0, 1.3, 1.6, 2.0 and 2.5 mA) were delivered from a constant current shock generator through a scrambler and were presented at thirty second intervals, within interseries interval of two minutes. Rats were observed for the presence of flinch (any observable response) or a jump (both hind paws leave the grid of the animal runs). The shock thresholds for each rat were defined as those shock intensities and elicited a flinch or jump response 50 percent of the time.

Four groups each of seven animals were injected interperntally with either water or 3-(p-trifluoromethylphenoxy)-N-methyl-3-phenylpropylamine dissolved in water at the levels indicated in Table 1. Each group of animals then were tested for shock threshold in a manner described above. The values given in Table 1 are the mean-jump threshold in milliamps.

TABLE 1

| Time | $H_2O$ (2ml/kk) | 3-(p-trifluoromethylphenoxy)-N-methyl-3-phenylpropylamine | | |
|---|---|---|---|---|
| | | 5 mg/kg | 10 mg/kg | 20 mg/kg |
| 2 hour | .72±.04 | .98±.08* | 1.08±.14* | 1.02±.05*** |
| 1 day | .72±.07 | 1.00±.03* | 1.15±.13* | 1.09±.06** |
| 2 day | .78±.07 | 1.03±.11 | 1.12±.07** | 1.17±.04*** |

*p<.05,
**p<.01,
***p<.001 compated to vehicle injected control group.

As shown in Table 1, analgesia is produced by the administration of 3-(p-trifluoromethylphenoxy-N-methyl-3-phenylpropylamine at concentrations between 5 mg/kg and 20 mg/kg. In addition, Table 1 shows that analgesia is produced even after two days following initial injection.

EXAMPLE 2

This examples illustrates that 3-(p-trifluoromethylphenoxy)-N-methyl-3-phenylpropylamine antagonizes the hyperalgesic effect of p-chlorophenylalanine.

Groups of rats were maintained and tested in accordance with the procedures set forth in Example 1. The threshold response and the number of rats in each group are shown in Table 2. Each group of rats was given an interparietale injection of either 4 ml/kg of a water vehicle adjusted to pH10 with sodium hydroxide 48 hours before testing or an injection of 300 mg/kg of p-chlorophenylalanine. Of the six groups of rats tested, two groups were injected subsequently with 2 ml/kg of the water vehicle and four groups were injecged with 3-(p-trifluoromethylphenoxy)-N-methyl-3-phenylpropylamine at the concentrations indicated in Table 2 and 2 hours before testing. The jump thresholds given in Table 2 are in milliamps.

TABLE 2

| 3-(p-trifluoromethylphenoxy)-N-methyl-3-phenylpropylamine (mg/kg) | $H_2O$ | pCPA (300 mg/kg) |
|---|---|---|
| 0 | .84±.04 (n=13) | .40±.06* (n=14) |
| 2.5 | .73±.06 (n=7) | .70±.06+ (n=7) |
| 20 | 1.28±.09* (n=7) | .75±.09+ (n=7) |

*p<.001 compared to vehicle injected control pump.
+p<.01 compared to pCPA injection group.

As shown in Table 2, the compounds 3-(p-trifluoromethylphenoxy)-N-methyl-3-phenylpropylamine inhibits the antagonistic action of p-chlorophenylamlimine. However, analgesia is not produced in the rat previously injected with the p-chlorophenylalimine. This contrast with prior art studies that show that para-chlorophenylamine antagonize the analgesic effect of morphine sulfate. Accordingly, this example provides substantial evidence that the compound of the 3-(p-trifluoromethylphenoxy)-N-methyl-3-phenylpropylamine produces analgesia by a mechanism different from the mechanism of morphine sulfate.

The measure 5-hydroxyinvoleacetic acide and serotonin, the rats were killed and brains and spinal cords were rapidly removed. Brains were dissected and the forebrain, midbrain and hindbrain sections and tissues were homogenized in acidified butanol. The supernatants were assayed for serotonin and its metabolite. The results are shown in Table 3 wherein the concentrations are in small mg/g.

TABLE 3

| Serotonin | Whole Brain | Forebrain | Midbrain | Hindbrain | Spinal Cord |
|---|---|---|---|---|---|
| $H_2O$ | 450±15 | 295±12 | 954±53 | 211±7 | 368±18 |
| 3PTNP | 457±10 | 331±8* | 1,137±48* | 233±8 | 400±13 |
| pCPA | — | 65±5** | 264±8** | 50±2** | 7±6** |
| pCPA + 3PTNP | — | 58±2 | 282±21 | 50±3 | 73±6 |

| 5 Hydroxyindoleacetic Acid | Whole Brain | Forebrain | Midbrain | Hindbrain | Spinal Cord |
|---|---|---|---|---|---|
| $H_2O$ | 454±8 | 424±10 | 654±30 | 253±12 | 219±12 |
| 3PTNP | 351±13** | 292±12** | 600±51 | 222±12 | 186±12 |
| pCPA | — | 68±8** | 137±7** | 84±8** | 60±7** |

TABLE 3-continued

| pCPA + 3PTNP | — | 47±2[+] | 310±13 | 59±4[++] | 59±11 |

[**]p<.001,
[*]p<.05 compared to vehicle injected control group.
[++]p<.01,
[+]p<.05 compated to pCPA injected group.

EXAMPLE 3

This example illustrates the effect of Naloxone on 3-(p-trifluoromethyl)-N-methyl-3-phenylpropylamine and the synergistic effect of that compound and morphine to produce analgesia.

Groups of 6 to 8 rats were injected with the phenyl propylamine compound (20 mg/kg, i.p.) or with water (2 ml/kg) 2 hours prior to testing. Naloxone (0.08 mg/kg, s.c.) and morphine sulfate (10 mg/kg, i.p.) or the water vehicle (1 ml/kg) were injected ½ hour prior to testing. Response was measured in the manner described in Example 1.

TABLE 4

| Drug | Jump Threshold (mA) (mean±S.E.M.) |
|---|---|
| vehicle | .81±.04 |
| phenylpropylamine | 1.15±.08 |
| Naloxone | .86±.14 |
| Naloxone+phenylpropylamine | 1.28±.09 |
| morphine | 1.10±.10 |
| Naloxone+morphine | .70±.05 |

TABLE 4-continued

| Drug | Jump Threshold (mA) (mean±S.E.M.) |
|---|---|
| morphine+phenylpropylamine | 1.88±.28 |

We claim:

1. The process for producing analgesia or reducing hyperalgesia in an animal which comprises administering a mixture of 3-(p-trifluoromethylphenoxy)-N-methyl-3-phenylpropylamine and morphine sulfate in an amount effective to produce analgesia or reduce hyperalgesia wherein the concentration of morphine sulfate comprises between about 25 to 50 weight percent of the 3-(p-trifluoromethylphenoxy)-N-methyl-3-phenylpropylamine.

2. The process of claim 1 wherein the animal is a human.

3. A composition comprising 3-(p-trifluoromethylphenoxy)-N-methyl-3-phenylpropylamine and morphine sulfate wherein the morphine sulfate comprises between about 25 and 50 weight percent of the 3-(p-trifluoromethylphenoxy)-N-methyl-3-phenylpropylamine.

* * * * *